(12) United States Patent
Job et al.

(10) Patent No.: US 9,404,066 B2
(45) Date of Patent: Aug. 2, 2016

(54) COLOUR PROTECTION DETERGENT

(71) Applicant: Henkel AG & Co. KGaA, Duesseldorf (DE)

(72) Inventors: Mareile Job, Leverkusen (DE); Birgit Gluesen, Duesseldorf (DE); John Taylor, Manchester (GB); Anthony Lawrence, Manchester (GB)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 14/946,322

(22) Filed: Nov. 19, 2015

(65) Prior Publication Data

US 2016/0075969 A1 Mar. 17, 2016

Related U.S. Application Data

(63) Continuation of application No. PCT/EP2014/059651, filed on May 12, 2014.

(30) Foreign Application Priority Data

May 22, 2013 (EP) ..................................... 13168795

(51) Int. Cl.

| C11D 3/26 | (2006.01) |
|---|---|
| C11D 3/32 | (2006.01) |
| C11D 3/37 | (2006.01) |
| C11D 3/00 | (2006.01) |
| C07C 275/04 | (2006.01) |
| C07C 275/26 | (2006.01) |
| C07C 275/28 | (2006.01) |

(52) U.S. Cl.
CPC ............ C11D 3/0021 (2013.01); C07C 275/04 (2013.01); C07C 275/26 (2013.01); C07C 275/28 (2013.01); C11D 3/32 (2013.01); C11D 3/323 (2013.01); C11D 3/3769 (2013.01); C11D 3/3776 (2013.01); C11D 3/3792 (2013.01)

(58) Field of Classification Search
CPC .. C11D 3/3776; C11D 3/3792; C11D 3/3769; C11D 3/32; C11D 3/0021; C07C 275/04; C07C 275/26; C07C 275/28; D06L 1/04
USPC ........ 510/276, 475, 501, 505; 8/137
See application file for complete search history.

(56) References Cited

U.S. PATENT DOCUMENTS 2,720,538 A   10/1955  Moessinger

FOREIGN PATENT DOCUMENTS

| EP | 0425427 A2 | 5/1991 |
|---|---|---|
| GB | 276337 | 8/1928 |
| GB | 1464427 | 2/1977 |
| GB | 1473201 | 5/1977 |
| GB | 1473202 | 5/1977 |
| GB | 1473571 | 5/1977 |

OTHER PUBLICATIONS

PCT International Search Report (PCT/EP2014/059651) dated Jul. 17, 2014.

*Primary Examiner* — Gregory R Delcotto
(74) *Attorney, Agent, or Firm* — Thomas G. Krivulka

(57) ABSTRACT

The present invention improves dye transfer inhibition in the washing of textiles by the use of urea derivatives comprising sulfonic or carboxylic acid groups.

11 Claims, No Drawings

COLOUR PROTECTION DETERGENT

FIELD OF THE INVENTION

The present invention generally relates to the use of urea derivatives as dye transfer-inhibiting active ingredients in the washing of textiles and to detergents which contain such compounds.

BACKGROUND OF THE INVENTION

In addition to the constituents essential for the washing process such as surfactants and builders, detergents generally contain further ingredients which may be grouped together under the heading of washing auxiliaries and thus include various groups of active ingredients such as foam regulators, graying inhibitors, bleaching agents, bleaching activators and enzymes. Such auxiliary substances also include substances which are intended to prevent dyed textiles from having a modified color appearance after washing. This change in color appearance of washed, i.e. clean, textiles may be due, on the one hand, to proportions of the dye being removed from the textile by the washing process ("fading"), and, on the other hand, to dyes dissolved out from differently colored textiles being deposited on the textile ("discoloration"). Change of the discoloration kind may also involve undyed items of washing if these are washed together with colored items of washing. In order to avoid these undesired side-effects of removing dirt from textiles by treatment with conventionally surfactant-containing aqueous systems, detergents, especially when they are intended as "color" detergents for washing colored textiles, contain active ingredients which are intended to prevent the dissolution of dyes from the textile or at least the deposition of dissolved-out dyes present in the washing liquor onto textiles. Many of the polymers conventionally used have such a high affinity for dyes that they draw them to a greater extent from the dyed fiber, such that greater color losses occur.

It has surprisingly now been found that certain urea derivatives with aromatic groups give rise to unexpectedly high dye transfer inhibition if they are used in detergents.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Detergent containing a dye transfer inhibitor in the form of a urea derivative of the general formula I,

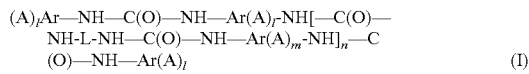   (I)

in which Ar denotes an aromatic group, a stilbene group, or a linear, branched, or cyclic, saturated or once or several times ethylenically unsaturated hydrocarbon group with 1 to 12 carbon atoms, optionally substituted by up to 3 alkyl substituents with 1 to 4 carbon atoms; L denotes an arylene or stilbene group, optionally substituted by up to 3 alkyl substituents with 1 to 5 carbon atoms and/or optionally substituted by up to 3 groups —$SO_3M$, or denotes an alkylene group with 2 to 4 carbon atoms; A denotes —$SO_3M$ or —$CO_2M$; M denotes H or an alkali metal atom; l and m irrespective of each other denote 0, 1, 2 or 3, and l+m≥1; and n denotes a number of from 1 to 6, in addition to conventional constituents compatible with this ingredient.

Use of urea derivatives of the general formula I,

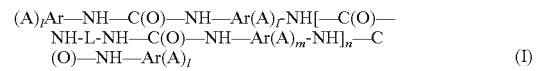   (I)

in which Ar denotes an aromatic group, a stilbene group, or a linear, branched, or cyclic, saturated or once or several times ethylenically unsaturated hydrocarbon group with 1 to 12 carbon atoms, optionally substituted by up to 3 alkyl substituents with 1 to 4 carbon atoms; L denotes an arylene or stilbene group, optionally substituted by up to 3 alkyl substituents with 1 to 5 carbon atoms and/or optionally substituted by up to 3 groups —$SO_3M$, or denotes an alkylene group with 2 to 4 carbon atoms; A denotes —$SO_3M$ or —$CO_2M$; M denotes H or an alkali metal atom; l and m irrespective of each other denote 0, 1, 2 or 3, and l+m≥1; and n denotes a number of from 1 to 6, for avoiding the transfer of textile dyes from dyed textiles onto undyed or differently colored textiles when they are jointly washed in aqueous solutions, in particular surfactant-containing aqueous solutions.

Use of urea derivatives of the general formula I,

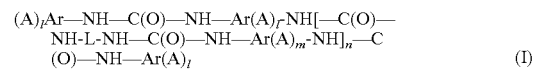   (I)

in which Ar denotes an aromatic group, a stilbene group, or a linear, branched, or cyclic, saturated or once or several times ethylenically unsaturated hydrocarbon group with 1 to 12 carbon atoms, optionally substituted by up to 3 alkyl substituents with 1 to 4 carbon atoms; L denotes an arylene or stilbene group, optionally substituted by up to 3 alkyl substituents with 1 to 5 carbon atoms and/or optionally substituted by up to 3 groups —$SO_3M$, or denotes an alkylene group with 2 to 4 carbon atoms; A denotes —$SO_3M$ or —$CO_2M$; M denotes H or an alkali metal atom; l and m irrespective of each other denote 0, 1, 2 or 3, and l+m≥1; and n denotes a number of from 1 to 6, for avoiding the modifying the color appearance of dyed textiles when they are washed in aqueous solutions, in particular surfactant-containing aqueous solutions.

Method for washing textiles in surfactant-containing aqueous solutions, wherein a surfactant-containing aqueous solution is used which contains a urea derivative of the general formula I,

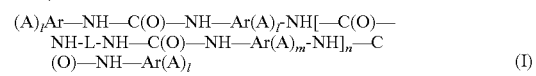   (I)

in which Ar denotes an aromatic group, a stilbene group, or a linear, branched, or cyclic, saturated or once or several times ethylenically unsaturated hydrocarbon group with 1 to 12 carbon atoms, optionally substituted by up to 3 alkyl substituents with 1 to 4 carbon atoms, L denotes an arylene or stilbene group, optionally substituted by up to 3 alkyl substituents with 1 to 5 carbon atoms and/or optionally substituted by up to 3 groups —$SO_3M$, or denotes an alkylene group with 2 to 4 carbon atoms, A denotes —$SO_3M$ or —$CO_2M$, M denotes H or an alkali metal atom, l and m irrespective of each other denote 0, 1, 2 or 3, and l+m≥1, and n denotes a number of from 1 to 6.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention provides the use of urea derivatives of the general formula I,

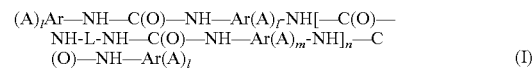   (I)

in which
Ar denotes an aromatic group, a stilbene group, or a linear, branched, or cyclic, saturated or once or several times ethylenically unsaturated hydrocarbon group with 1 to 12 carbon atoms, optionally substituted by up to 3 alkyl substituents with 1 to 4 carbon atoms,
L denotes an arylene or stilbene group, optionally substituted by up to 3 alkyl substituents with 1 to 5 carbon atoms and/or optionally substituted by up to 3 groups —SO₃M, or denotes an alkylene group with 2 to 4 carbon atoms,
A denotes —SO₃M or —CO₂M,
M denotes H or an alkali metal atom,
l and m irrespective of each other denote 0, 1, 2 or 3, and l+m≥1
n denotes a number of from 1 to 6, preferably from 2 to 6,
for avoiding the transfer of textile dyes from dyed textiles onto undyed or differently colored textiles when they are jointly washed in aqueous solutions, in particular surfactant-containing aqueous solutions.

matic, as for example toluene diisocyanate (TDI), 4,4' methylene diphenyl diisocyanate (MDI), and phenyldisocyanate. Mixtures of the stated substances may also be used. Alternatively, sulfonic acid substituents may be introduced into the polymer by sulfonating the polymer subsequent to the polymerization of monomers. The urea derivatives of the general formula I may also be obtained by reacting the corresponding amines with phosgene.

Preferably the average molecular weight (here and in the following: weight average) of the compounds according to general formula I is in the range of from 1000 g/mol to 4000 g/mol, in particular in the range of from 1000 g/mol to 2000 g/mol.

Preferred urea derivatives according to general formula I are those of formula II,

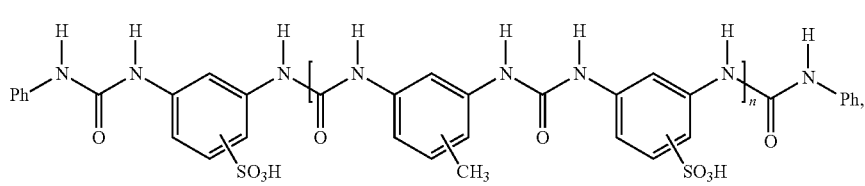

The preventive action against the staining of white or also differently colored textiles by dyes washed out of the textiles is particularly pronounced when the textile is made of or comprises polyamide. It is conceivable that the urea derivatives attach themselves to the textiles during washing and have a repellent action on the dye molecules present in the in which Ph is a phenyl group, n is 1, 2, 3, or 4, the substituents —SO₃H are in ortho positions, and the substituent —CH₃ is in ortho position. Any of the sulfonic acid groups may assume alkali metal salt form, if one so wishes.

Other preferred urea derivatives according to general formula I are those of formula III,

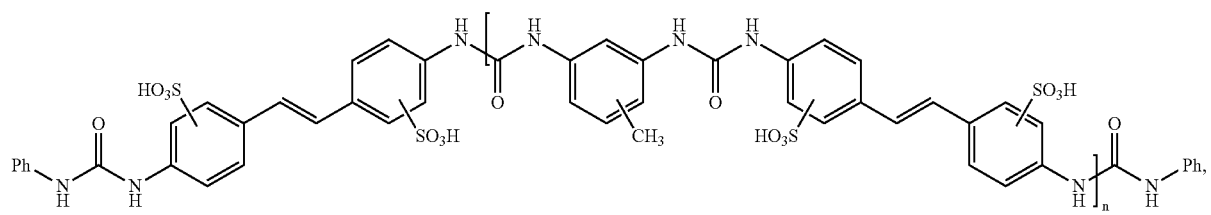

liquor, which is especially pronounced when they comprise sulfonic or carboxylic acid group substituents.

The present invention also provides a color protective detergent containing a dye transfer inhibitor in the form of a urea derivative of the above-stated general formula I in addition to conventional constituents compatible with this ingredient.

Ar in the compounds of general formula I preferably is selected from the group encompassing phenyl, naphthyl, stilbyl, kresyl, and mixtures thereof. L in the compounds of general formula I preferably is selected from the group encompassing toluylene, methylenediphenylene, and mixtures thereof. The index m in the compounds of general formula I preferably is 1. The index n in the compounds of general formula I may be an integer or a fractional number, and preferably is in the range of from 2 to 4.

Urea derivatives of the general formula I are obtainable by reacting optionally sulfonic acid and/or carboxylic acid bearing diamines with isocyanates and diisocyanates. The amines are preferably aromatic, as for example diamino benzene, diamino naphthalene, and diamino stilbene, which may bear one ore more additional carboxylic and/or, preferably, sulfonic acid groups. The isocyanates are preferably aromatic, as for example phenyl isocyanate, naphthyl isocyanate, and stilbenyl isocyanate. The diisocyanates are also preferably aroin which Ph is a phenyl group, n is 1, 2, 3, or 4, the substituents —SO₃H are in ortho positions, and the substituent —CH₃ is in ortho position. Any of the sulfonic acid groups may assume alkali metal salt form, if one so wishes.

A detergent according to the invention preferably contains 0.05 wt. % to 2 wt. %, in particular 0.2 wt. % to 1 wt. %, of dye transfer-inhibiting compound of the general formula I as defined above.

The compounds of the general formula I make a contribution to both of the above-mentioned aspects of color consistency, i.e. they reduce both discoloration and fading, although the staining prevention effect, in particular when washing white textiles, is most pronounced. The present invention accordingly also provides the use of a corresponding compound for avoiding the modification of the color appearance of textiles when they are washed in aqueous solutions, in particular surfactant-containing aqueous solutions. A modification of the color appearance should not be taken to mean the difference between the dirty and the clean textile, but instead the difference between the clean textile in each case before and after the washing operation.

The present invention also provides a method for washing dyed textiles in surfactant-containing aqueous solutions, wherein a surfactant-containing aqueous solution is used which contains a compound of the general formula I. In such a method, it is possible also to wash white or undyed textiles together with the dyed textile without the white or undyed textile being stained.

A detergent according to the invention may, in addition to the compound according to formula I, contain a known dye transfer inhibitor, preferably in quantities of 0.1 wt. % to 2 wt. %, in particular 0.2 wt. % to 1 wt. %, said inhibitor being in a preferred development of the invention a polymer of vinylpyrrolidone, vinylimidazole, vinylpyridine N-oxide or a copolymer thereof. Usable compounds are not only the polyvinylpyrrolidones with a molecular weight of for example 15,000 g/mol to 50,000 g/mol but also the polyvinylpyrrolidones with a molecular weight of above 1,000,000 g/mol, in particular of 1,500,000 g/mol to 4,000,000 g/mol, N-vinylimidazole/N-vinylpyrrolidone copolymers, polyvinyl-oxazolidones, copolymers based on vinyl monomer and carboxamides. It is, however, also possible to use enzymatic systems comprising a peroxidase and hydrogen peroxide or a substance which releases hydrogen peroxide in wate. The addition of a mediator compound for the peroxidase, for example an acetosyringone or a phenothiazine or phenoxazine is preferred in this case, it also additionally being possible to use the above-stated polymeric dye transfer inhibitor active ingredients. For use in detergents according to the invention, polyvinylpyrrolidone preferably has an average molar mass in the range from 10,000 g/mol to 60,000 g/mol, in particular in the range from 25,000 g/mol to 50,000 g/mol. Preferred copolymers are those prepared from vinylpyrrolidone and vinylimidazole in the molar ratio 5:1 to 1:1 having an average molar mass in the range from 5,000 g/mol to 50,000 g/mol, in particular 10,000 g/mol to 20,000 g/mol.

The detergents according to the invention, which may in particular assume the form of pulverulent solids, post-compacted particles, homogeneous solutions or suspensions, may in principle, apart from the active ingredient used according to the invention, contain any constituents which are known and conventional in such products. The detergents according to the invention may in particular contain builder substances, surfactants, bleaching agents based on organic and/or inorganic peroxy compounds, bleaching activators, water-miscible organic solvents, enzymes, sequestering agents, electrolytes, pH regulators and further auxiliary materials, such as optical brighteners, graying inhibitors, foam regulators together with colorants and fragrances.

The detergents according to the invention may contain one surfactant or two or more surfactants, it being possible in particular to consider not only anionic surfactants, nonionic surfactants and mixtures thereof, but also cationic, zwitterionic and amphoteric surfactants.

Suitable nonionic surfactants are in particular alkylglycosides and ethoxylation and/or propoxylation products of alkylglycosides or linear or branched alcohols in each case having 12 to 18 C atoms in the alkyl moiety and 3 to 20, preferably 4 to 10, alkyl ether groups. Corresponding ethoxylation and/or propoxylation products of N-alkylamino, vicinal diols, fatty acid esters and fatty acid amides, which correspond with regard to the alkyl moiety to the stated long-chain alcohol derivatives, and of alkylphenols having 5 to 12 C atoms in the alkyl residue may furthermore be used.

Preferably used nonionic surfactants are alkoxylated, advantageously ethoxylated, in particular primary alcohols with preferably 8 to 18 C atoms and on average 1 to 12 mol of ethylene oxide (EO) per mol of alcohol, in which the alcohol residue may be linear or preferably methyl-branched in position 2 or may contain linear and methyl-branched residues in the mixture, as are conventionally present in oxo alcohol residues. In particular, however, alcohol ethoxylates with linear residues prepared from alcohols of natural origin with 12 to 18 C atoms, for example from coconut, palm, tallow fat or oleyl alcohol, and on average 2 to 8 EO per mol of alcohol are preferred. Preferred ethoxylated alcohols include, for example, $C_{12}$-$C_{14}$ alcohols with 3 EO or 4 EO, $C_9$-$C_{11}$ alcohols with 7 EO, $C_{13}$-$C_{15}$ alcohols with 3 EO, 5 EO, 7 EO or 8 EO, $C_{12}$-$C_{18}$ alcohols with 3 EO, 5 EO or 7 EO and mixtures of these, such as mixtures of $C_{12}$-$C_{14}$ alcohol with 3 EO and $C_{12}$-$C_{18}$ alcohol with 7 EO. The stated degrees of ethoxylation are statistical averages which, for a specific product, may be an integer or a fractional number. Preferred alcohol ethoxylates have a narrow homologue distribution (narrow range ethoxylates, NRE). In addition to these nonionic surfactants, fatty alcohols with more than 12 EO may also be used. Examples of these are (tallow) fatty alcohols with 14 EO, 16 EO, 20 EO, 25 EO, 30 EO or 40 EO. In particular in products for use in machine washing, extremely low-foam compounds are conventionally used. These preferably include $C_{12}$-$C_{18}$ alkylpolyethylene glycol/polypropylene glycol ethers in each case having up to 8 mol of ethylene oxide and propylene oxide units per molecule. It is, however, also possible to use other nonionic surfactants which are known to be low-foaming, such as for example $C_{12}$-$C_{18}$-alkyl polyethylene glycol/polybutylene glycol ethers with in each case up to 8 mol ethylene oxide and butylene oxide units per molecule and end group-terminated alkylpolyalkylene glycol mixed ethers. Alkoxylated alcohols containing hydroxyl groups, or "hydroxy mixed ethers", are also particularly preferred. Alkylglycosides of the general formula $RO(G)_x$, in which R means a primary linear or methyl-branched aliphatic residue, in particular methyl-branched in position 2, with 8 to 22, preferably 12 to 18 C atoms, and G denotes a glycose unit with 5 or 6 C atoms, preferably glucose, may also be used as nonionic surfactants. The degree of oligomerization x, which indicates the distribution of monoglycosides and oligoglycosides, is any desired number and, being an analytically determined variable, may also assume fractional values between 1 and 10; x is preferably 1.2 to 1.4. Polyhydroxy fatty acid amides of the formulae (IV) and (V) are likewise suitable, in which $R^1$ and $R^3$ denote linear or branched alkyl or alkenyl residues with 7 to 12 carbon atoms, $R^2$ denotes hydrogen, an alkyl or hydroxyalkyl residue with 1 to 4 carbon atoms, $R^4$ denotes a linear, branched or cyclic alkylene residue or an arylene residue with 2 to 8 carbon atoms, $R^5$ denotes a linear, branched or cyclic alkyl residue or an aryl residue or an oxyalkyl residue with 1 to 8 carbon atoms, $C_1$-$C_4$ alkyl or phenyl residues being preferred, and [Z] denotes a linear or branched polyhydroxyalkyl residue with 3 to 10 carbon atoms, the alkyl chain of which is substituted with at least two hydroxyl groups, or alkoxylated, preferably ethoxylated or propoxylated, derivatives of this residue:

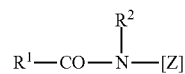

(IV)

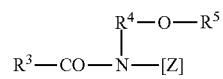

(V)

The polyhydroxy fatty acid amides, especially those of formula (V), may preferably be derived from reducing sugars with 5 or 6 carbon atoms. [Z] is also preferably obtained by reductive amination of a sugar such as glucose, fructose, maltose, lactose, galactose, mannose or xylose. The N-alkoxy- or N-aryloxy-substituted compounds may then be converted into the desired polyhydroxy fatty acid amides by reaction with fatty acid methyl esters in the presence of an alkoxide as catalyst. A further class of preferably used nonionic surfactants, which are used either as sole nonionic surfactant or in combination with other nonionic surfactants, in particular together with alkoxylated fatty alcohols and/or alkyl glycosides, are alkoxylated, preferably ethoxylated or ethoxylated and propoxylated fatty acid alkyl esters, preferably with 1 to 4 carbon atoms in the alkyl chain, in particular fatty acid methyl esters. Nonionic surfactants of the amine oxide type, for example N-coconut alkyl-N,N-dimethylamine oxide and N-tallow alcohol-N,N-dihydroxyethylamine oxide, and the fatty acid alkanolamide type may also be suitable. The quantity of these nonionic surfactants preferably amounts to no more than that of the ethoxylated fatty alcohols, in particular no more than half the quantity thereof. "Gemini" surfactants may also be considered as further surfactants. These are generally taken to mean such compounds as have two hydrophilic groups per molecule. These groups are generally separated from one another by a "spacer". This spacer is generally a carbon chain which should be long enough for the hydrophilic groups to be sufficiently far apart that they can act mutually independently. Such surfactants are in general distinguished by an unusually low critical micelle concentration and the ability to bring about a great reduction in the surface tension of water. In exceptional cases, gemini surfactants include not only such "dimeric" surfactants, but also corresponding "trimeric" surfactants. Suitable gemini surfactants are, for example, sulfated hydroxy mixed ethers or dimer alcohol bis- and trimer alcohol tris-sulfates and -ether sulfates. End group-terminated dimeric and trimeric mixed ethers are in particular distinguished by their di- and multifunctionality. The stated end group-terminated surfactants accordingly exhibit good wetting characteristics and are low-foaming, such that they are in particular suitable for use in machine washing or cleaning processes. Gemini polyhydroxy fatty acid amides or poly-polyhydroxy fatty acid amides may, however, also be used.

Suitable anionic surfactants are in particular soaps and those which contain sulfate or sulfonate groups. Surfactants of the sulfonate type which may preferably be considered are $C_9$-$C_{13}$ alkyl benzene sulfonates, olefin sulfonates, i.e. mixtures of alkene and hydroxyalkane sulfonates and disulfonates, as are obtained, for example, from $C_{12}$-$C_{18}$ monoolefins with a terminal or internal double bond by sulfonation with gaseous sulfur trioxide and subsequent alkaline or acidic hydrolysis of the sulfonation products. Alkane sulfonates which are obtained from $C_{12}$-$C_{18}$ alkanes for example by sulfochlorination or sulfoxidation with subsequent hydrolysis or neutralization are also suitable. The esters of α-sulfo fatty acids (ester sulfonates), for example the α-sulfonated methyl esters of hydrogenated coconut, palm kernel or tallow fatty acids, which are produced by α-sulfonation of the methyl esters of fatty acids of vegetable and/or animal origin with 8 to 20 C atoms in the fatty acid molecule and subsequent neutralization to yield water-soluble mono salts, may also be considered suitable. The α-sulfonated esters of hydrogenated coconut, palm, palm kernel or tallow fatty acids are here preferred, it also being possible for sulfonation products of unsaturated fatty acids, for example oleic acid, also to be present in small quantities, preferably in quantities of no more than approx. 2 to 3 wt. %. Preferred α-sulfo fatty acid alkyl esters are in particular those which comprise an alkyl chain with no more than 4 C atoms in the ester group, for example methyl ester, ethyl ester, propyl ester and butyl ester. The methyl esters of α-sulfo fatty acids (MES), and the saponified disalts thereof too, are particularly advantageously used. Further suitable anionic surfactants are sulfated fatty acid glycerol esters, which are mono-, di- and triesters and mixtures thereof, as are obtained during production by esterification by a monoglycerol with 1 to 3 mol of fatty acid or on transesterification of triglycerides with 0.3 to 2 mol of glycerol. Preferred alk(en)yl sulfates are the alkali metal and in particular sodium salts of sulfuric acid semi-esters of $C_{12}$-$C_{18}$ fatty alcohols for example prepared from coconut fatty alcohol, tallow fatty alcohol, lauryl, myristyl, cetyl- or stearyl alcohol or $C_{10}$-$C_{20}$ oxo alcohols and those semi-esters of secondary alcohols of this chain length. Alk(en)yl sulfates of the stated chain length which contain a synthetic linear alkyl residue produced on a petrochemical basis and which exhibit degradation behavior similar to that of the appropriate compounds based on fatty chemical raw materials are also preferred. In particular, $C_{12}$-$C_{16}$ alkyl sulfates and $C_{12}$-$C_{15}$ alkyl sulfates and $C_{14}$-$C_{15}$ alkyl sulfates are preferred because of their washing characteristics. 2,3-Alkyl sulfates, which may be obtained as commercial products of Shell Oil Company under the name DAN®, are also suitable anionic surfactants. The sulfuric acid monoesters of linear or branched $C_7$-$C_{21}$ alcohols ethoxylated with 1 to 6 mol of ethylene oxide are also suitable, such as 2-methyl-branched $C_9$-$C_{11}$ alcohols with on average 3.5 mol of ethylene oxide (EO) or $C_{12}$-$C_{18}$ fatty alcohols with 1 to 4 EO. Preferred anionic surfactants also include the salts of alkylsulfosuccinic acid, which are also known as sulfosuccinates or sulfosuccinic acid esters, and are the monoesters and/or diesters of sulfosuccinic acid with alcohols, preferably fatty alcohols and in particular ethoxylated fatty alcohols. Preferred sulfosuccinates contain $C_8$ to $C_{18}$ fatty alcohol residues or mixtures thereof. Particularly preferred sulfosuccinates contain a fatty alcohol residue which is derived from ethoxylated fatty alcohols, which are in themselves nonionic surfactants. Sulfosuccinates whose fatty alcohol residues are derived from ethoxylated fatty alcohols with a narrow homologue distribution are here particularly preferred. It is likewise also possible to use alk(en)ylsuccinic acid with preferably 8 to 18 carbon atoms in the alk(en)yl chain or the salts thereof. Further anionic surfactants which may be considered are fatty acid derivatives of amino acids, for example of N-methyltaurine (taurides) and/or of N-methylglycine (sarcosides). Sarcosides or sarcosinates are particularly preferred here and most especially sarcosinates of higher and optionally mono- or polyunsaturated fatty acids such as oleyl sarcosinate. Further anionic surfactants which may in particular be considered are soaps. Saturated fatty acid soaps are in particular suitable, such as the salts of lauric acid, myristic acid, palmitic acid, stearic acid, hydrogenated erucic acid and behenic acid and in particular soap mixtures derived from natural fatty acids, for example coconut, palm kernel or tallow fatty acids. Known alkenylsuccinic acid salts may also be used together with these soaps or as substitutes for soaps.

The anionic surfactants, including the soaps, may be present in the form of the sodium, potassium or ammonium salts thereof and as soluble salts of organic bases, such as mono-, di- or triethanolamine. The anionic surfactants are preferably present in the form of the sodium or potassium salts thereof, in particular in the form of the sodium salts.

Surfactants are present in detergents according to the invention in amounts of preferably 5 wt. % to 50 wt. %, in particular of 8 wt. % to 30 wt. %.

A detergent according to the invention preferably contains at least one water-soluble and/or water-insoluble, organic and/or inorganic builder. The water-soluble organic builder substances include polycarboxylic acids, in particular citric acid and saccharic acids, monomeric and polymeric aminopolycarboxylic acids, in particular methylglycinediacetic acid, nitrilotriacetic acid and ethylenediaminetetraacetic acid and polyaspartic acid, polyphosphonic acids, in particular aminotris(methylenephosphonic acid), ethylenediaminetetrakis(methylenephosphonic acid) and 1-hydroxyethyl-1,1-diphosphonic acid, polymeric hydroxy compounds such as dextrin and polymeric (poly)carboxylic acids, in particular polycarboxylates obtainable by oxidation of polysaccharides or dextrins, polymeric acrylic acids, methacrylic acids, maleic acids and copolymers thereof, which may also contain small proportions of polymerizable substances without carboxylic acid functionality incorporated therein by polymerization. The relative molecular mass of the homopolymers of unsaturated carboxylic acids is in general between 3,000 and 200,000, that of the copolymers between 2,000 and 200,000, preferably 30,000 to 120,000, in each case relative to free acid. One particularly preferred acrylic acid/maleic acid copolymer has a relative molecular mass of 30,000 to 100,000. Conventional commercial products are for example Sokalan® CP 5, CP 10 and PA 30 from BASF. Suitable, albeit less preferred, compounds of this class are copolymers of acrylic acid or methacrylic acid with vinyl ethers, such as vinyl methyl ethers, vinyl esters, ethylene, propylene and styrene, the acid fraction of which amounts to at least 50 wt. %. Terpolymers containing as monomers two unsaturated acids and/or the salts thereof and, as third monomer, vinyl alcohol and/or an esterified vinyl alcohol or a carbohydrate may also be used as water-soluble organic builder substances. The first acidic monomer or the salt thereof is derived from a monoethylenically unsaturated $C_3$-$C_8$-carboxylic acid and preferably from a $C_3$-$C_4$-monocarboxylic acid, in particular from (meth)acrylic acid. The second acidic monomer or the salt thereof may be a derivative of a $C_4$-$C_8$-dicarboxylic acid, maleic acid being particularly preferred, and/or a derivative of an allylsulfonic acid which is substituted in position 2 with an alkyl or aryl residue. Such polymers generally have a relative molecular mass of between 1,000 and 200,000. Further preferred copolymers are those which comprise acrolein and acrylic acid/acrylic acid salts or vinyl acetate as monomers. The organic builder substances may be used, in particular for producing liquid products, in the form of aqueous solutions, preferably in the form of 30 to 50 wt. % aqueous solutions. All the stated acids are generally used in the form of the water-soluble salts, in particular the alkali metal salts, thereof.

Such organic builder substances may, if desired, be present in quantities of up to 40 wt. %, in particular of up to 25 wt. % and preferably of 1 wt. % to 8 wt. %. Quantities close to the stated upper limit are preferably used in pasty or liquid, in particular water-containing, detergents according to the invention.

Water-soluble inorganic builder materials which may in particular be considered are alkali metal silicates, alkali metal carbonates and alkali metal phosphates, which may be present in the form of the alkaline, neutral or acidic sodium or potassium salts thereof. Examples of these are trisodium phosphate, tetrasodium diphosphate, disodium dihydro gendiphosphate, pentasodium triphosphate, "sodium hexametaphosphate", oligomeric trisodium phosphate with degrees of oligomerization of 5 to 1000, in particular 5 to 50, and the corresponding potassium salts or mixtures of sodium and potassium salts. Water-insoluble, water-dispersible inorganic builder materials which are used are in particular crystalline or amorphous alkali metal aluminosilicates, in quantities of up to 50 wt. %, preferably of no more than 40 wt. % and, in liquid products, in particular from 1 wt. % to 5 wt. %. Preferred such materials are crystalline sodium aluminosilicates of detergent grade, in particular zeolite A, P and optionally X, alone or in mixtures, for example in the form of a co-crystallization product of zeolites A and X (Vegobond® AX, a commercial product of Condea Augusta S.p.A.). Quantities close to the stated upper limit are preferably used in solid, particulate products. Suitable aluminosilicates in particular comprise no particles with a grain size of above 30 µm and preferably consist to an extent of at least 80 wt. % of particles with a size below 10 µm. Their calcium binding capacity, which may be determined as stated in German patent DE 24 12 837, is generally in the range from 100 to 200 mg of CaO per gram.

Suitable substitutes or partial substitutes for the stated aluminosilicates are crystalline alkali metal silicates, which may be present alone or mixed with amorphous silicates. The alkali metal silicates usable as builders in the products according to the invention preferably have a molar ratio of alkali metal oxide to $SiO_2$ of below 0.95, in particular of 1:1.1 to 1:12 and may be in amorphous or crystalline form. Preferred alkali metal silicates are sodium silicates, in particular amorphous sodium silicates, with an $Na_2O$:$SiO_2$ molar ratio of 1:2 to 1:2.8. Those with an $Na_2O$:$SiO_2$ molar ratio of 1:1.9 to 1:2.8 may be produced in accordance with the method of European patent application EP 0 425 427. Preferably used crystalline silicates, which may be present alone or mixed with amorphous silicates, are crystalline phyllosilicates of the general formula $Na_2Si_xO_{2x+1} \cdot y\ H_2O$, in which x, or "modulus", is a number from 1.9 to 22, in particular 1.9 to 4 and y is a number from 0 to 33 and preferred values for x are 2, 3 or 4. Preferred crystalline phyllosilicates are those in which x in the stated general formula assumes the values 2 or 3.

In particular, both β- and δ-sodium disilicates ($Na_2Si_2O_5 \cdot y\ H_2O$) are preferred. Virtually anhydrous crystalline alkali metal silicates of the above-stated general formula in which x means a number from 1.9 to 2.1, which are produced from amorphous alkali metal silicates, may be used in detergents according to the invention. A crystalline sodium phyllosilicate with a modulus of 2 to 3, as may be produced from sand and soda, is used in a further preferred embodiment of detergents according to the invention. Crystalline layered silicates of the above-stated formula (I) are commercially available from Clariant GmbH under the trade name Na-SKS, for example Na-SKS-1 ($Na_2Si_{22}O_{45} \times H_2O$, kenyaite), Na-SKS-2 ($Na_2Si_{14}O_{29} \times H_2O$, magadiite), Na-SKS-3 ($Na_2Si_8O_{17} \times H_2O$) or Na-SKS-4 ($Na_2Si_4O_9 \times H_2O$, makatite). Suitable representatives of these are primarily Na-SKS-5 (α-$Na_2Si_2O_5$), Na-SKS-7 (β-$Na_2Si_2O_5$, natrosilite), Na-SKS-9 ($NaHSi_2O_5 \cdot 3H_2O$), Na-SKS-10 ($NaHSi_2O_5 \cdot 3H_2O$, kanemite), Na-SKS-11 (t-$Na_2Si_2O_5$) and Na-SKS-13 ($NaHSi_2O_5$), but in particular Na-SKS-6 (δ-$Na_2Si_2O_5$). In a preferred development of detergents according to the invention, a granular compound is used which is prepared from crystalline phyllosilicate and citrate, from crystalline phyllosilicate and above-stated (co)polymeric polycarboxylic acid, or from alkali metal silicate and alkali metal carbonate, as is commercially available for example under the name Nabion® 15.

Builder substances are preferably present in detergents according to the invention in quantities of up to 75 wt. %, in particular of 5 wt. % to 50 wt. %.

Peroxy compounds suitable for use in detergents according to the invention which may in particular be considered are organic peracids or peracid salts of organic acids, such as phthalimidopercaproic acid, perbenzoic acid or salts of diperdodecanedioic acid, hydrogen peroxide and inorganic salts which release hydrogen peroxide under washing conditions, which latter include perborate, percarbonate, persilicate and/or persulfate such as caroate. Where solid peroxy compounds are to be used, they may be used in the form of powders or granules, which may also in principle be encapsulated in known manner. If a product according to the invention contains peroxy compounds, these are preferably present in quantities of up to 50 wt. %, in particular of 5 wt. % to 30 wt. %. It may be appropriate to add relatively small quantities of known bleaching agent stabilizers, such as for example phosphonates, borates or metaborates and metasilicates and magnesium salts such as magnesium sulfate.

Bleaching activators which may be used are compounds which, under perhydrolysis conditions, yield aliphatic peroxycarboxylic acids with preferably 1 to 10 C atoms, in particular 2 to 4 C atoms, and/or optionally substituted perbenzoic acid. Suitable substances are those which bear O- and/or N-acyl groups having the stated number of C atoms and/or optionally substituted benzoyl groups. Preferred substances are repeatedly acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate, 2,5-diacetoxy-2,5-dihydrofuran and enol esters and acetylated sorbitol and mannitol, or the mixtures thereof (SORMAN), acylated sugar derivatives, in particular pentaacetyl glucose (PAG), pentaacetyl fructose, tetraacetyl xylose and octaacetyl lactose and acetylated, optionally N-alkylated glucamine and gluconolactone, and/or N-acylated lactams, for example N-benzoylcaprolactam. Such bleaching activators may be present, in particular in the presence of the above-stated hydrogen peroxide-releasing bleaching agents, in a conventional quantity range, preferably in quantities of 0.5 wt. % to 10 wt. %, in particular 1 wt. % to 8 wt. %, relative to the entire product, but are preferably entirely absent when percarboxylic acid is used as the sole bleaching agent.

In addition to or instead of the above listed conventional bleaching activators, sulfone imines and/or bleach-boosting transition metal salts or transition metal complexes may be present as "bleach catalysts".

Enzymes usable in the products which may be considered are those from the class of amylases, proteases, lipases, cutinases, pullulanases, hemicellulases, cellulases, oxidases, laccases and peroxidases and mixtures thereof. Particularly suitable enzymatic active ingredients are those obtained from fungi or bacteria, such as *Bacillus subtilis, Bacillus licheniformis, Bacillus lentus, Streptomyces griseus, Humicola lanuginosa, Humicola insolens, Pseudomonas pseudoalcaligenes, Pseudomonas cepacia* or *Coprinus cinereus*. The enzymes may be adsorbed onto carrier substances and/or be embedded in encapsulating substances in order to protect them from premature inactivation. They are present in the washing or cleaning products according to the invention preferably in quantities of up to 5 wt. %, in particular of 0.2 wt. % to 4 wt. %. If the product according to the invention contains protease, it preferably exhibits a proteolytic activity in the range from approx. 100 PU/g to approx. 10,000 PU/g, in particular 300 PU/g to 8000 PU/g. If two or more enzymes are to be used in the product according to the invention, this may be achieved by incorporating the two or more separate enzymes or enzymes which are separately formulated in known manner or by two or more enzymes jointly formulated in a granular product.

Organic solvents other than water which may be used in the detergents according to the invention, in particular if these are in liquid or pasty form, include alcohols with 1 to 4 C atoms, in particular methanol, ethanol, isopropanol and tert.-butanol, diols with 2 to 4 C atoms, in particular ethylene glycol and propylene glycol, and mixtures thereof and the ethers derivable from the stated classes of compounds. Such water-miscible solvents are preferably present in the products according to the invention in quantities of no more than 30 wt. %, in particular of 6 wt. % to 20 wt. %.

In order to establish a desired pH value which is not automatically obtained by mixing the remaining components, the detergents according to the invention may contain acids which are compatible with the system and are environmentally compatible, in particular citric acid, acetic acid, tartaric acid, malic acid, lactic acid, glycolic acid, succinic acid, glutaric acid and/or adipic acid, as well as mineral acids, in particular sulfuric acid, or bases, in particular ammonium or alkali metal hydroxides. Such pH regulators are present in the detergents according to the invention in quantities of preferably no more than 20 wt. %, in particular of 1.2 wt. % to 17 wt. %.

Graying inhibitors have the task of keeping dirt which has been dissolved away from the textile fibers suspended in the liquor. Water-soluble colloids of a mainly organic nature are suitable for this purpose, for example starch, size, gelatin, salts of ether carboxylic acids or ether sulfonic acids of starch or cellulose or salts of acidic sulfuric acid esters of cellulose or starch. Water-soluble polyamides containing acidic groups are also suitable for this purpose. Derivatives of starch other than those stated above, for example aldehyde starches, may further be used. Cellulose ethers, such as carboxymethylcellulose (Na salt), methylcellulose, hydroxyalkylcellulose and mixed ethers, such as methylhydroxyethylcellulose, methylhydroxypropylcellulose, methylcarboxymethylcellulose and mixtures thereof, are preferably used, for example in quantities of 0.1 to 5 wt. %, relative to the detergent.

Textile detergents according to the invention may for example contain derivatives of diaminostilbene disulfonic acid or the alkali metal salts thereof as optical brighteners, although they preferably contain no optical brightener for use as a color detergent. Suitable compounds are, for example, salts of 4,4'-bis(2-anilino-4-morpholino-1,3,5-triazinyl-6-amino)stilbene 2,2'-disulfonic acid or compounds of similar structure which, instead of the morpholino group, bear a diethanolamino group, a methylamino group, an anilino group or a 2-methoxyethylamino group. Brighteners of the substituted diphenylstyryl type may furthermore be present, for example the alkali metal salts of 4,4'-bis(2-sulfostyryl)-diphenyl, 4,4'-bis(4-chloro-3-sulfostyryl)-diphenol, or 4-(4-chlorostyryl)-4'-(2-sulfostyryl)-diphenyl. Mixtures of the above-stated optical brighteners may also be used.

Especially for use in machine washing, it may be advantageous to add conventional foam inhibitors to the products. Suitable foam inhibitors are, for example, soaps of natural or synthetic origin, which comprise an elevated proportion of $C_{18}$-$C_{24}$ fatty acids. Suitable non-surfactant foam inhibitors are, for example, organopolysiloxanes and mixtures thereof with microfine, optionally silanized silica as well as paraffins, waxes, microcrystalline waxes and mixtures thereof with silanized silica or bistearylethylenediamides. Mixtures of different foam inhibitors are also advantageously used, for example mixtures of silicones, paraffins or waxes. The foam inhibitors, in particular foam inhibitors containing silicone and/or paraffin, are preferably bound to a granular carrier substance which is soluble or dispersible in water. Mixtures of paraffins and bistearylethylenediamide are particularly preferred here.

The production of solid detergents according to the invention presents no difficulties and may proceed in known manner, for example by spray drying or granulation, with enzymes and any further thermally sensitive constituents such as for example bleaching agents optionally subsequently being separately added. Products according to the invention with an elevated bulk density, in particular in the range from 650 g/l to 950 g/l, may preferably produced by a method comprising an extrusion step. A further preferred production process is using a granulation method.

Detergents according to the invention may preferably be produced in the form of tablets, which may be monophasic or multiphasic, single-colored or multicolored and in particular consist of one layer or of two or more, in particular two, layers, by mixing together all the ingredients, optionally for each layer, in a mixer and compression molding the mixture by means of conventional tablet presses, for example eccentric presses or rotary presses, with pressing forces in the range from approx. 50 to 100 kN, preferably at 60 to 70 kN. In particular in the case of multilayer tablets, it may be advantageous for at least one layer to be preliminarily compression molded. This is preferably carried out at pressing forces of between 5 and 20 kN, in particular at 10 to 15 kN. In this manner, breaking-resistant tablets are straightforwardly obtained which nevertheless dissolve sufficiently rapidly under conditions of use and exhibit breaking and flexural strength values usually of 100 to 200 N, but preferably of above 150 N. A tablet produced in this manner is preferably of a weight of 10 g to 50 g, in particular of 15 g to 40 g. The tablets may be of any desired three-dimensional shape and may be round, oval or polygonal, intermediate shapes also being possible. Corners and edges are advantageously rounded. Round tablets preferably have a diameter of 30 mm to 40 mm. In particular the size of polygonal or cuboidal tablets, which are predominantly introduced by means of the dispenser for example of a dishwashing machine, is dependent on the geometry and volume of this dispenser. Preferred embodiments have, for example, a base area of (20 to 30 mm)×(34 to 40 mm), in particular of 26×36 mm or of 24×38 mm.

Liquid or pasty detergents according to the invention in the form of solutions containing conventional solvents are generally produced by simply mixing the constituents, which may be introduced into an automatic mixer as an undissolved material or as a solution.

EXAMPLES

Example 1

Syntheses of Urea Derivatives

Compound A 2,4-Diaminobenzenesulfonic acid (28.2 g, 0.15 mol) was dissolved in water (400 ml) by the addition of sodium bicarbonate (12.6 g, 0.15 mol). Acetone (200 ml) was added followed by phenylisocyanate (11.9 g, 0.10 mol) and the mixture was stirred for 16 h. The mixture was clarified through a glass fibre filter to remove a small amount of insoluble white solid and gave a clear pale yellow solution. Further acetone (200 ml) was added followed by tolylene-2,4-diisocyanate (15.7 g, 0.09 mol) and the mixture was stirred for 24 h. The mixture was again filtered to remove insoluble solids and the filtrate was concentrated in vacuo to leave a viscous brown liquid. The organic content was approximated from the C and N values determined by combustion analysis, based on an estimated empirical formula of $C_{2.41}H_{2.09}N_{0.58}Na_{0.15}O_{0.73}S_{0.15}$, calculated from the molar ratio and molecular formula of materials added to the reaction. $C_{2.41}H_{2.09}N_{0.58}Na_{0.15}O_{0.73}S_{0.15}$ requires C, 49.0%; N, 13.7%. Typically, values of C, 19.6-24.5% and N, 5.5-6.9% were found, giving a typical organic content of 40-50%.

Compound B 2,4-Diaminobenzenesulfonic acid (28.2 g, 0.15 mol) was dissolved in water (500 ml) by the addition of sodium bicarbonate (12.6 g, 0.15 mol). Acetone (250 ml) was added followed by tolylene-2,4-diisocyanate (17.4 g, 0.10 mol) and the mixture was stirred for 16 h. The mixture was clarified through a glass fibre filter to remove a small amount of insoluble white solid and gave a clear pale yellow solution. Further acetone (250 ml) was added followed by phenylisocyanate (12.0 g, 0.10 mol) and the mixture was stirred for 24 h. The mixture was again filtered to remove insoluble solids and the filtrate was concentrated in vacuo to leave a viscous brown liquid. The organic content was approximated from the C and N values determined by combustion analysis, based on an estimated empirical formula of $C_{2.50}H_{2.15}N_{0.60}Na_{0.15}O_{0.75}S_{0.15}$, calculated from the molar ratio and molecular formula of materials added to the reaction. $C_{2.50}H_{2.15}N_{0.60}Na_{0.15}O_{0.75}S_{0.15}$ requires C, 49.3%; N, 13.8%. Typically, values of C, 19.7-24.7% and N, 5.5-6.9% were found, giving a typical organic content of 40-50%.

Compound C (E)-6,6'-(Ethene-1,2-diyl)bis(3-aminobenzenesulfonic acid) (55.6 g, 0.15 mol) was dissolved in water (600 ml) by the addition of sodium bicarbonate (25.2 g, 0.30 mol). Acetone (300 ml) was added followed by tolylene-2,4-diisocyanate (17.4 g, 0.10 mol) and the mixture was stirred vigorously for 4 h. Phenyl isocyanate (10.7 g, 0.09 mol) was then added and the mixture was stirred for 24 h. The mixture was heated to 90° C. and filtered to remove insoluble solids. The filtrate was concentrated in vacuo to leave a viscous brown liquid. The organic content was approximated from the C and N values determined by combustion analysis, based on an estimated empirical formula of $C_{3.63}H_{2.85}N_{0.59}Na_{0.30}O_{1.19}S_{0.30}$, calculated from the molar ratio and molecular formula of materials added to the reaction. $C_{3.63}H_{2.85}N_{0.59}Na_{0.3}O_{1.19}S_{0.30}$ requires C, 48.3%; N, 9.2%. Values of C, 12.7% and N, 2.4% were found, giving a typical organic content of 26%.

As an alternative to concentrating in vacuo, the filtrate, after clarification, can be freeze dried to produce a beige powder.

Compound D (E)-6,6'-(Ethene-1,2-diyl)bis(3-aminobenzenesulfonic acid) (55.6 g, 0.15 mol) was dissolved in water (400 ml) by the addition of sodium bicarbonate (25.2 g, 0.30 mol). Acetone (200 ml) was added followed by phenyl isocyanate (11.9 g, 0.10 mol) and the mixture was stirred for 16 h. Tolylene-2,4-diisocyanate (15.7 g, 0.09 mol) was added and the mixture was stirred for a further 24 h. The mixture was filtered to remove insoluble solids and the filtrate was concentrated in vacuo to leave a viscous amber liquid. The organic content was approximated from the C and N values determined by combustion analysis, based on an estimated empirical formula of $C_{3.61}H_{2.84}N_{0.58}Na_{0.30}O_{1.18}S_{0.30}$, calculated from the molar ratio and molecular formula of materials added to the reaction. $C_{3.61}H_{2.84}N_{0.58}Na_{0.30}O_{1.18}S_{0.30}$ requires C, 48.3%; N, 9.1%. Values of C, 15.8% and N, 3.0% were found, giving a typical organic content of 33%.

As an alternative to concentrating in vacuo, the filtrate, after clarification, can be freeze dried to produce a yellow powder.

Compound E (E)-6,6'-(Ethene-1,2-diyl)bis(3-aminobenzenesulfonic acid) (55.6 g, 0.15 mol) was dissolved in water (600 ml) by the addition of sodium bicarbonate (25.2 g, 0.30 mol). Acetone (300 ml) was added followed by 4,4'-methylenebis (phenyl isocyanate) (25.0 g, 0.10 mol). The mixture was stirred at ambient temp. for 30 minutes then heated to 45° C. for 1 h. After allowing to cool to 25° C., phenyl isocyanate (11.9 g, 0.10 mol) was added and the mixture was stirred for 24 h. The mixture was filtered to remove a small amount insoluble solid and the filtrate was concentrated by evaporation in an open vessel at 80° C., to leave a viscous amber liquid, which solidifies on cooling. The organic content was approximated from the C and N values determined by combustion analysis, based on an estimated empirical formula of $C_{4.3}H_{3.3}N_{0.6}Na_{0.3}O_{1.2}S_{0.3}$, calculated from the molar ratio and molecular formula of materials added to the reaction. $C_{4.3}H_{3.3}N_{0.6}Na_{0.3}O_{1.2}S_{0.3}$ requires C, 52.1%; N, 8.5%. Values of C, 22.7% and N, 3.7% were found, giving a typical organic content of 44%.

As an alternative to concentrating in vacuo, the filtrate, after clarification, can be freeze dried to produce a yellow powder.

Example 2

Dye Transfer Inhibition

Compounds A, B, C, and D, produced according to the preceeding example, were added to a laundry liquor comprising a liquid detergent (LD) without dye transfer inhibitor, in the amounts (% by weight) given in the following tables. White textiles made of polyamide (PA, acceptor) or Cotton (CA, acceptor) in the presence of a poorly dyed textile (bleeder) were washed therein at 60° C. for 30 minutes, using water of hardness 16° d. Staining of the white textile was measured according to ISO 105 A04 and rated on a scale from 1 (=severely stained) to 5 (=no discernible staining), as given in the following tables:

| Dye Transfer Inhibition | | SSR value, ISO 105 A04 | | | |
|---|---|---|---|---|---|
| acceptor | bleeder | LD | 5% A | 2.5% A | 10% B |
| PA | BL1 | 1.8 | 4.1 | 3.3 | 3.5 |
| | BL2 | 3.0 | 4.6 | 4.3 | 4.4 |
| | BL3 | 3.1 | 4.1 | 3.8 | 4.1 |

| Dye Transfer Inhibition | | SSR value, ISO 105 A04 | | | | | | |
|---|---|---|---|---|---|---|---|---|
| acceptor | bleeder | LD | 3% C | 1% C | 0.5% C | 5% D | 1% D | 5% E |
| PA | BL1 | 1.7 | 4.5 | 3.8 | 3.0 | 4.4 | 2.9 | 4.7 |
| | BL2 | 2.6 | 4.9 | 4.7 | 4.5 | 4.8 | 4.5 | 4.8 |
| | BL3 | 2.8 | 3.3 | 3.2 | 3.1 | 3.3 | 3.1 | 3.5 |
| CO | BL1 | 4.3 | 4.9 | 4.8 | 4.8 | 5.0 | 4.8 | 4.8 |

As bleeders were used
BL1: Acid Blue 113, EMPA 131
BL2: Direct Orange 39, EMPA 134
BL3: Disperse Blue 79, AISE 41-31

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Detergent comprising a dye transfer inhibitor in the form of a urea derivative of the general formula I, $$(A)_l\text{-Ar-NH-C(O)-NH-Ar(A)}_l\text{-NH[-C(O)-NH-L-NH-C(O)-NH-Ar(A)}_m\text{-NH]}_n\text{-C(O)-NH-Ar(A)}_l \quad (I)$$

in which
Ar denotes an aromatic group, a stilbene group, or a linear, branched, or cyclic, saturated or once or several times ethylenically unsaturated hydrocarbon group with 1 to 12 carbon atoms;

L denotes an arylene or stilbene group;
A denotes —SO$_3$M or —CO$_2$M;
M denotes H or an alkali metal atom;
l and m irrespective of each other denote 0, 1, 2 or 3, and l+m≥1;
n denotes a number of from 1 to 6.

2. Detergent according to claim 1, wherein Ar of general formula I is selected from the group consisting of phenyl, naphthyl, stilbyl, kresyl, and mixtures thereof.

3. Detergent according to claim 1, wherein L of general formula I is selected from the group consisting of toluylene, methylenediphenylene, and mixtures thereof.

4. Detergent according to claim 1, wherein m of general formula I is 1.

5. Detergent according to claim 1, wherein n of general formula I is in the range of from 2 to 4.

6. Detergent according to claim 1, wherein the average molecular weight of the compounds according to general formula I is in the range of from 1000 g/mol to 4000 g/mol.

7. Detergent according to claim 1, wherein the urea derivative of general formula I is of formula II,

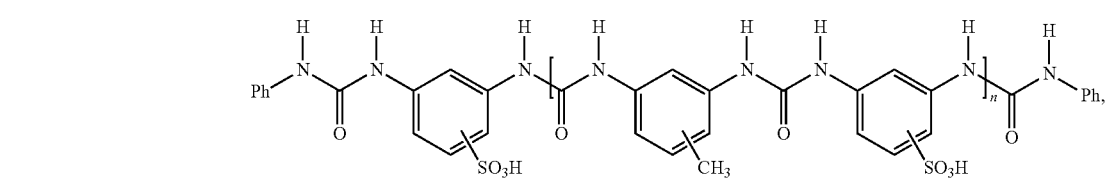

in which Ph is a phenyl group, n is 1, 2, 3, or 4, the substituents —SO$_3$H are in ortho positions, and the substituent —CH$_3$ is in ortho position.

8. Detergent according to claim 1, wherein the urea derivative of general formula I is of formula III,

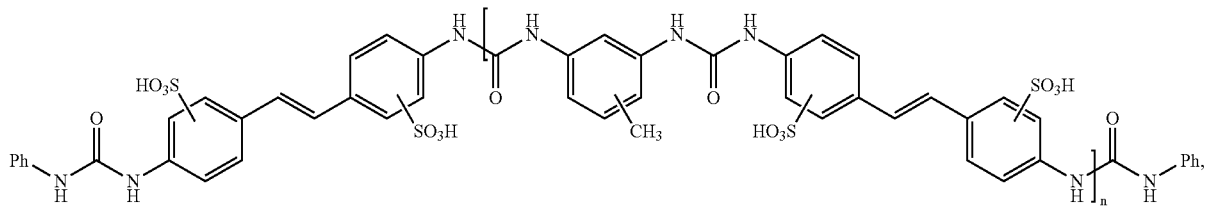

in which Ph is a phenyl group, n is 1, 2, 3, or 4, the substituents —SO₃H are in ortho positions, and the substituent —CH₃ is in ortho position.

9. Detergent according to claim 1, wherein the detergent comprises 0.1 wt. % to 10 wt. %, of the dye transfer-inhibiting urea derivative.

10. Detergent according to claim 1, wherein the detergent further comprises a polymer of vinylpyrrolidone, vinylimidazole, vinylpyridine N-oxide or a copolymer thereof.

11. Method for washing textiles in a surfactant-containing aqueous solution, wherein a surfactant-containing aqueous solution is contacted with said textiles and comprises a urea derivative of the general formula I,

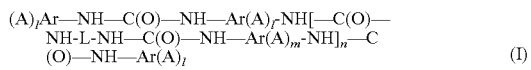

in which
Ar denotes an aromatic group, a stilbene group, or a linear, branched, or cyclic, saturated or once or several times ethylenically unsaturated hydrocarbon group with 1 to 12 carbon atoms,
L denotes an arylene or stilbene group,
A denotes —SO₃M or —CO₂M,
M denotes H or an alkali metal atom,
l and m irrespective of each other denote 0, 1, 2 or 3, and l+m≥1
n denotes a number of from 1 to 6.

* * * * *